(12) United States Patent
Cho (10) Patent No.: US 8,500,649 B2
(45) Date of Patent: Aug. 6, 2013

(54) BLOOD PRESSURE MEASURING APPARATUS AND METHOD FOR MEASURING BLOOD VESSEL ELASTICITY

(75) Inventor: Jae-Geol Cho, Yongin-si (KR)

(73) Assignee: Samsung Electronics Co., Ltd (KR)

( * ) Notice: Subject to any disclaimer, the term of this patent is extended or adjusted under 35 U.S.C. 154(b) by 218 days.

(21) Appl. No.: 12/974,751

(22) Filed: Dec. 21, 2010

(65) Prior Publication Data
US 2011/0152699 A1   Jun. 23, 2011

(30) Foreign Application Priority Data

Dec. 21, 2009   (KR) ...................... 10-2009-00128505

(51) Int. Cl.
*A61B 5/02* (2006.01)

(52) U.S. Cl.
USPC ......................................... 600/490; 600/483

(58) Field of Classification Search
None
See application file for complete search history.

(56) References Cited

U.S. PATENT DOCUMENTS

| 2006/0264771 | A1* | 11/2006 | Lin et al. ........................ 600/513 |
| 2008/0027330 | A1* | 1/2008 | Naghavi et al. ................ 600/481 |
| 2010/0130876 | A1* | 5/2010 | Cho .............................. 600/490 |

FOREIGN PATENT DOCUMENTS

| JP | 2002-136489 | 5/2002 |
| JP | 2004-236730 | 8/2004 |
| JP | 2005-152449 | 6/2005 |
| KR | 1020060069032 | 6/2006 |

OTHER PUBLICATIONS

The Changes in Pulse Transit Time at Specific Cuff Pressures During Inflation and Deflation, Liu et al.*
Compariative Effects of Aging in Men and Women on the Properties of the Arterial Tree, Smulyan et al.*
D.J. Hughes et al., "Measurements of Young's Modulus of Elasticity of the Canine Aorta with Ultrasound", Ultrasonic Imaging 1, 356-367 (1979).

* cited by examiner

*Primary Examiner* — Michael Kahelin
*Assistant Examiner* — Mitchell Alter
(74) *Attorney, Agent, or Firm* — The Farrell Law Firm, P.C.

(57) ABSTRACT

A blood pressure measuring method which can measure blood vessel elasticity, so that that the blood vessel elasticity can be commonly applied to all subjects, calculating pulse transit time at the time when no pressure is applied, calculating pulse transit time in an area where the pressure is changed by the cuff, and then calculating the elasticity of a blood vessel, using the pulse transit times.

16 Claims, 6 Drawing Sheets

BLOOD PRESSURE MEASURING APPARATUS AND METHOD FOR MEASURING BLOOD VESSEL ELASTICITY

PRIORITY

This application claims priority to an application entitled "Blood Pressure Measuring Apparatus and Method for Measuring Blood Vessel Elasticity" filed in the Korean Intellectual Property Office on Dec. 21, 2009, and assigned Serial No. 10-2009-0128505, the entire disclosure of which is incorporated herein by reference.

BACKGROUND OF THE INVENTION

1. Field of the Invention

The present invention generally relates to a blood pressure measuring apparatus and method, and more particularly to a blood pressure measuring apparatus and method for measuring blood vessel elasticity.

2. Description of the Related Art

Recently, as concern for health has increased, it has become possible for a person to measure the state of his/her health using various medical devices. As a result, a subject can measure their own bio-signals, such as blood pressure, heart rate, pulse and the like. Specifically, in order to prevent hypertension (high blood pressure) or the like, it is important to regularly check the state of the blood vessels. This can be accomplished by checking for diseases, such as atherosclerosis (thickening of artery walls).

Figure 1:
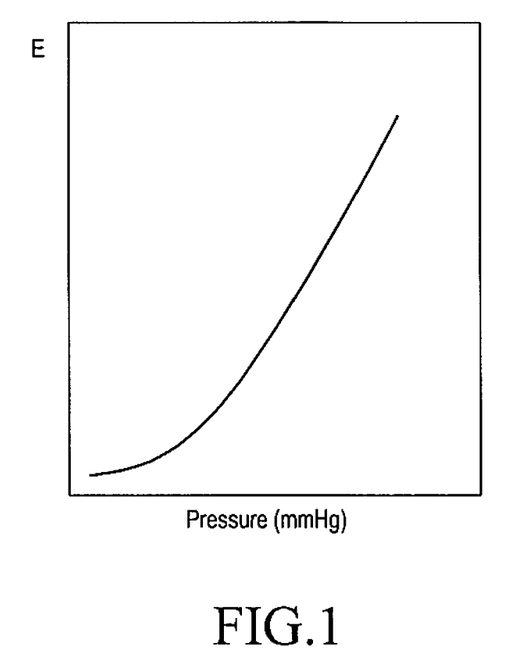
FIG. 1 illustrates a typical Young's modulus of an artery in terms of pressure.

It may be said that the blood vessel health may be indicated by arterial stiffness, i.e., how much the inner wall of an artery is thickened and how much its distensibility (elasticity) is lost due to the accumulation of foreign matter on its inner wall. Arterial stiffness may be estimated by measuring blood vessel elasticity. FIG. 1 illustrates a Young's modulus (a measure of stiffness) of an artery in relation to pressure, from which it can be seen that as pressure increases, the Young's modulus E increases exponentially. Since the physical meaning of E is blood vessel elasticity required for increasing a unit diameter, it can be seen that if the y-intercept is constant, force required to increase the diameter of the same artery increases as the slope of the graph becomes steeper. In other words, in FIG. 1, the steeper slope of the graph indicates higher arterial stiffness, and the lower blood vessel elasticity, wherein E may be typically expressed as follows:

$$E = E_o \exp(\alpha P) \quad (1)$$

In Equation (1), $E_0$ and $\alpha$ are constants, exp( ) stands for an exponential function, and P is internal pressure of a blood vessel, wherein if E is expressed in this exponential form, it may be said that the blood vessel elasticity according to pressure change is determined by the constant $\alpha$. Since it is not easy to directly measure E or $\alpha$ of a human artery, blood vessel elasticity measuring methods using Pulse Wave Velocity (PWV) are widely used as blood vessel elasticity measuring methods.

Figure 2:
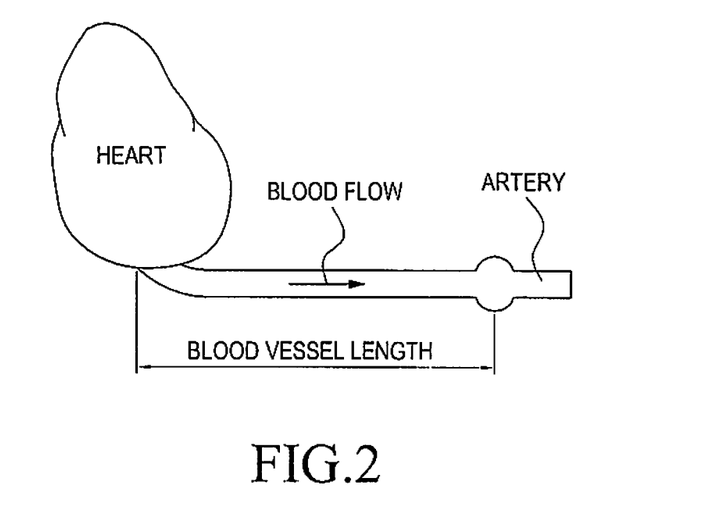
FIG. 2 is illustrates a typical pulse wave time.

In order to describe such a method using PWV, reference is made to FIG. 2. FIG. 2 illustrates a general relationship between Pulse Transit Time (PTT) and PWV. As shown in FIG. 2, the pulse transit time is defined by the time required for an arterial pulse to arrive at a peripheral point, such as a fingertip or a toe, starting from the heart, and the PWV is obtained by dividing the vascular length by the PIT. The PWV may be expressed as Equation (2) below, wherein since a function of Young's modulus E is employed, the PWV will generally indicate a higher value as the blood vessel elasticity decreases. In particular, the PWV in an aorta is generally known as an early detection indicator for aging of blood vessels, arteriosclerosis, hypertension, diabetes, hyperlipidemia, renal disease, and the like.

$$PWV = \sqrt{\frac{Eh}{2\rho R}} \quad (2)$$

In Equation (2), R is blood vessel radius, h is blood vessel wall thickness, and p is blood density. In Equation (2), as the blood vessel wall thickness increases, the PWV also increases, from which it can be seen that the PWV may vary depending on blood pressure, blood vessel diameter, and blood vessel wall thickness.

As described above, the PWV varies depending on the internal pressure of an artery, and also depends on characteristics, such as blood vessel wall thickness, blood vessel radius, and blood density, which are varied from person to person. Therefore, unless the PWV is measured for the same blood vessel at the same blood pressure, it is impossible to evaluate the absolute blood vessel elasticity using the PWV. That is, through the measurement of PWV, it is impossible to determine that the blood vessel elasticity is high as compared to another person, it is only possible to merely confirm that the blood vessel elasticity is improving or worsening when the PWV is continuously measured for the same individual at the same blood pressure.

SUMMARY OF THE INVENTION

Accordingly, the present invention has been made to solve the above-mentioned problems occurring in the prior art, and the present invention provides a blood pressure measuring apparatus and method which can measure blood vessel elasticity so that the blood vessel elasticity is applicable to all subjects.

Also, the present invention provides a blood pressure measuring apparatus and method to easily and conveniently measure blood vessel elasticity.

In accordance with an aspect of the present invention, there is provided a blood pressure measuring apparatus for measuring blood vessel elasticity, including a Pulse Wave Velocity (PWV) measuring module for measuring PWV, using an electrocardiogram signal and a pulse wave signal; a blood pressure measuring module for measuring blood pressure by pressurizing or decompressing a cuff; and a control unit, wherein the control unit calculates initial pulse transit time, using the PWV at the time when the cuff is not pressurized, the control unit calculates pulse transit time in a pressure applied cuff area when the pressure is applied by the cuff, and the control unit calculates blood vessel elasticity, using the initial pulse transit time and the pulse transit time in the pressure applied cuff area.

In accordance with another aspect of the present invention, there is provided a blood pressure measuring method for measuring blood vessel elasticity by a blood pressure measuring apparatus, including measuring pulse wave velocity (PWV), using an electrocardiogram signal and a pulse wave signal; measuring blood pressure by pressurizing or decompressing a cuff; calculating initial pulse transit time, using the PWV at the time when the cuff is not pressurized; calculating pulse transit time in a pressure applied cuff area when the pressure is applied by the cuff; and calculating blood vessel elasticity, using the initial pulse transit time and the pulse transit time in the pressure applied cuff area.

BRIEF DESCRIPTION OF THE DRAWINGS

The above and other aspects, features and advantages of the present invention will be more apparent from the following detailed description taken in conjunction with the accompanying drawings, in which:

FIGS. 4a to 4c illustrate the relationships between cuff pressures used at the time of measuring blood pressure used in the present invention and pulse transit time measurement results, respectively;

DETAILED DESCRIPTION OF THE EMBODIMENTS OF THE PRESENT INVENTION

Hereinafter, embodiments of the present invention will be described with reference to the accompanying drawings. In the following description, the same elements will be designated by the same reference numerals although they are shown in different drawings. Further, various definitions found in the following description, such as specific values of packet identifications, contents of displayed information, and the like, are provided only to help with the general understanding of the present invention, and it is apparent to those skilled in the art that the present invention can be implemented without such definitions. Further, in the following description of the present invention, a detailed description of known functions and configurations incorporated herein will be omitted when it may make the subject matter of the present invention unclear.

The present invention provides a blood pressure measuring method which can measure blood vessel elasticity, so that that the blood vessel elasticity can be commonly applied to all subjects. For this purpose, considering that wave transit time varies depending on cuff pressure, the present invention includes calculating pulse transit time when no pressure is applied, calculating pulse transit time in an area where the pressure is changed by a cuff, and then calculating the elasticity of blood vessel using the calculated pulse transit times. By using the pulse transit times related to blood vessel elasticity in this manner, it is possible to determine the blood vessel elasticity which can be used as an absolute indicator irrespective of the blood pressure and individual variation.

Figure 3:
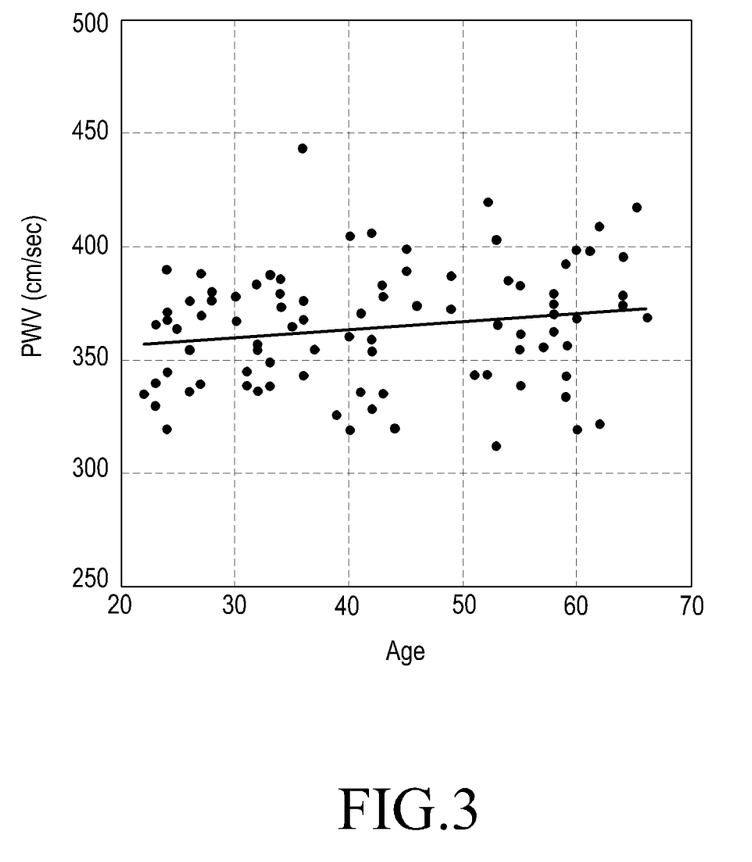
FIG. 3 illustrates measured pulse wave velocity values for individual Korean women by age groups.

Before describing the present invention, reference is made to FIG. 3 so as to illustrate the characteristics of PWV. FIG. 3 is a graph showing measured PWV values for individual Korean women who have a cardiovascular disease, such as atherosclerosis or hypertension, by age groups. It is well known in general that as a person gets older, his or her arterial stiffness increases, and as shown in FIG. 3, there is a tendency for PWV to increase as age increases. However, since the PWV also varies depending on individual physical characteristics, such as blood vessel diameter and blood vessel wall thickness, and blood pressure, its variation from person to person is very high, and is widely distributed as shown in FIG. 3. As a result, such a PWV measuring method is not suitable to be used as an absolute indicator of blood vessel elasticity. Therefore, another method is required which can be used as an absolute indicator of blood vessel elasticity.

Figure 4A:
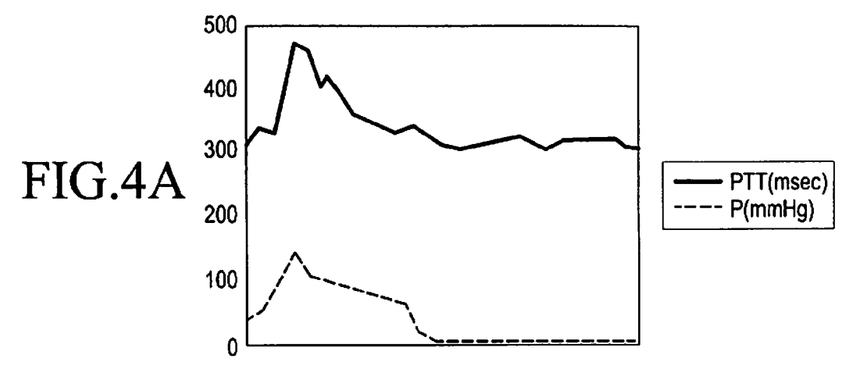
Figure 4B:
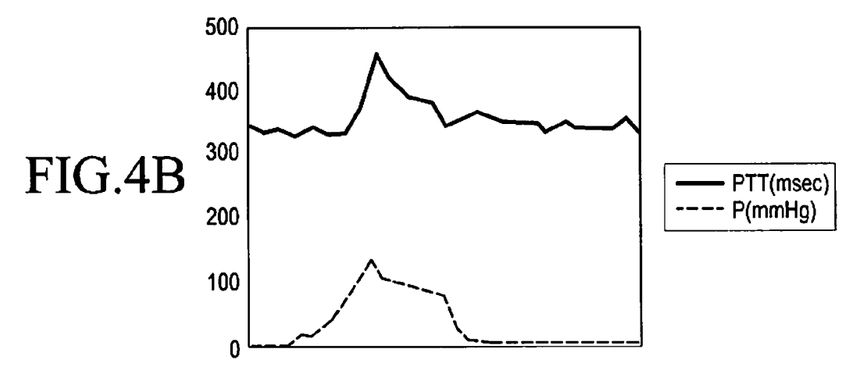
Figure 4C:
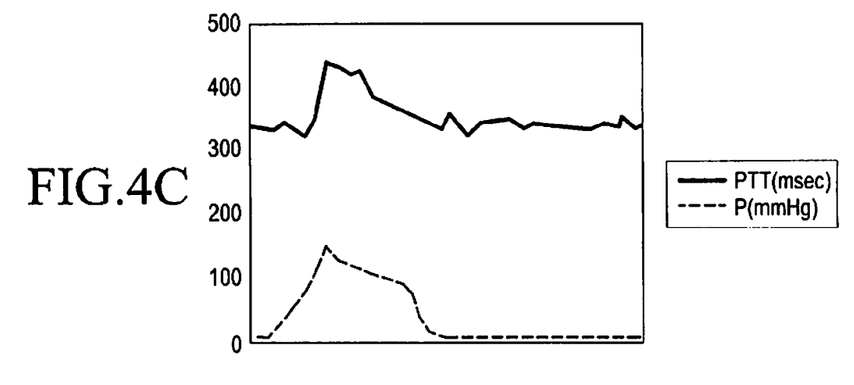

Thus, the present invention uses a characteristic that the pulse transit time varies according to cuff pressure. FIGS. 4a to 4c are graphs showing the relationships between Cuff Pressures (P) (mmHg) at the time of measuring blood pressure used in the present invention and Pulse Transit Time (PTT) (msec) measurement results, respectively. As shown in FIGS. 4a to 4c, as cuff pressure P increases, pulse transit time tends to increase. Here, pulse transit time is a length of time required for blood to arrive at an extremity, such as a fingertip or a toe, starting from the heart, and is calculated on the basis of an Electrocardiogram (ECG) signal and a pulse wave signal.

Such pulse transit time depends on transmural pressure (i.e., the difference in pressure between two sides of a wall), blood vessel thickness, blood vessel diameter, and blood vessel elasticity, wherein if the transmural pressure is changed by the cuff pressure, the pulse transit time is also changed. Pressure P in Equation 1 above stands for transmural pressure, which is obtained from the difference between blood pressure and pressure applied from the outside (i.e., cuff pressure). Therefore, if there is no cuff, the transmural pressure will be equal to the mean blood pressure, but if cuff pressure increases, the transmural pressure will decrease, and if the cuff pressure continuously increases and becomes equal to the mean blood pressure, the transmural pressure will become zero.

Therefore, if the cuff pressure increases, the transmural pressure P in Equation 1 above and the E in Equation 2 above will decrease. As a result, the pulse transit time will increase and the PWV will decrease). As the cuff pressure increases, the pulse transit time also increases.

The blood vessel length extends from the heart to an extremity where the pulse wave is measured. If the following are calculated, it is possible to determine the blood vessel elasticity of each subject, more exactly the constant α in Equation (1) above, using the PTT (pulse transit time) values measured according to the change of cuff pressure: (1) pulse transit time when no pressure is applied, (2) the length of pressure-applied area when pressure is applied, and when the pressure is applied, and (3) the pulse transit time in the pressure-applied.

Figure 5:
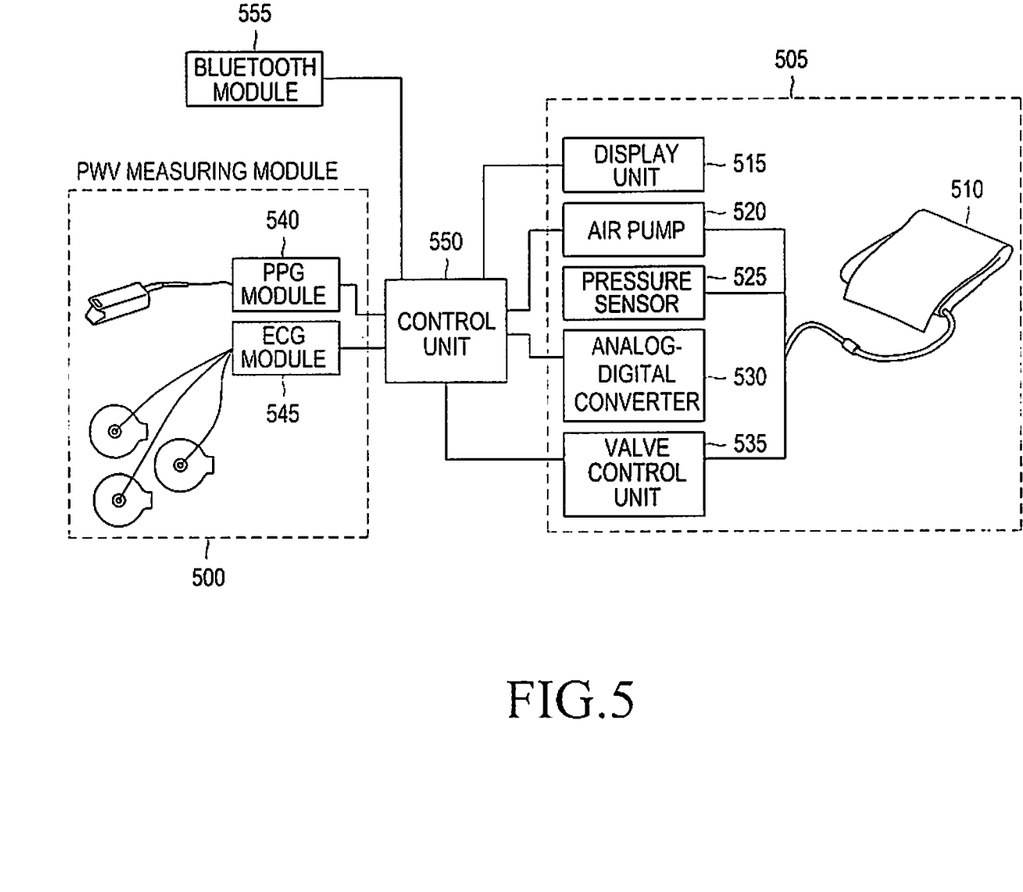
FIG. 5 is a block diagram illustrating internal operations of a blood pressure measuring apparatus for measuring blood vessel elasticity in accordance with an embodiment of the present invention.

In order to implement the above-mentioned function, the present invention proposes a blood pressure measuring apparatus including a PTT measuring sensor in addition to an oscillometry type electronic blood pressure measuring apparatus. FIG. 5 is a block diagram of the inner configuration of a blood pressure measuring apparatus for measuring blood vessel elasticity in accordance with an embodiment of the present invention.

Referring to FIG. 5, the blood pressure measuring apparatus is generally divided into a PWV measuring module 500, and a Blood Pressure (BP) measuring module 505.

Referring to the BP measuring module 505, the BP measuring module 505 has a construction similar to that of an oscillometry type sphygmomanometer. The BP measuring module 505 performs the operations of measuring blood pressure from oscillation occurring while pressurizing/decompressing an artery using a cuff 510, and estimating the cuff pressure at a time when the pulse waves by heartbeat have the maximum amplitude as mean blood pressure. The BP measuring module 505 includes a display unit 515, an air pump 520, a pressure sensor 525, an analog-digital converter 530, and a valve control unit 535.

Specifically, the cuff 510 is a means for cutting off or controlling arterial flow, the display unit 515 indicates a BP measuring result, blood vessel elasticity or the like, the air pump 520 pressurizes the cuff 510, and the pressure sensor 525 detects and converts pressure into an electronic signal through the analog-digital converter 530. The valve control unit 535 serves to decompress the cuff 510 in a desired rate, such that the valve control unit 535 may be configured to be capable of being manually or automatically controlled.

The PWV measuring module 500 is generally divided into a PhotoPlethysmoGraphy (PPG) module 540 and an (ECG) module 545. The PPG module 540 is a sensor for photoplethysmography of a subject, i.e. for detecting a PWV, wherein a clip type optical sensor adapted to be put on a fingertip may be used as the PPG module. Such an optical sensor consists of at least one light source for making light be incident to the skin so as to measure a pulse wave signal, and at least one optical detector for detecting light exiting from the skin as the light is scattered after being incident to the skin. The pulse wave signal is transferred to a control unit 550 to calculate the PTT. Additionally, the ECG module 545 receives a heartbeat signal of a subject through heartbeat electrodes, and transfers the heartbeat signal to the control unit 550. Although patch type electrodes are shown as the heartbeat electrodes, and a finger clip sensor is shown as the pulse wave measuring sensor in FIG. 5, other sensors capable of performing the same functions can be employed instead of the electrodes and the sensor.

Additionally, a Bluetooth® module 555 may be added to the inventive BP measuring apparatus as a wireless transceiver so that the calculated BP values, blood vessel information and the like can be supplied to a subject, using a communication medium, such as a portable phone, a Personal Digital Assistant (PDA) or a Personal Computer (PC). Moreover, the BP measuring apparatus of the present invention may include an input unit (not shown) to which information, such as a user's sex, height or the like may be input when calculating PTT, and may receive the information through the Bluetooth® module 555.

For example, the BP measuring apparatus may be mounted in the following manner. The cuff 510 is wrapped around an upper arm of a subject, the optical sensor is mounted on a fingertip of the cuff-wrapped arm, and the electrodes for measuring heartbeat are mounted on the subject's body, preferably to come into contact with the arms or hands of the subject. By mounting the components of the BP measuring apparatus in this manner, it is possible to measure PWV simultaneously with measuring the BP of the subject.

The control unit 550 calculates PTT, using the heartbeat signal measured by the ECG module 545, and the pulse wave signal measured by the PPG module 540. Here, the PTT is calculated by dividing the length of blood vessel L by PWV. Such PTT measurement can be continuously or intermittently performed through the control of the air pump 520 and the valve control unit 535. The PTT may be expressed by Equation (3) below.

$$PTT = \frac{L}{PWV} = L\sqrt{\frac{2\rho R}{E_o h}} \exp\left(-\frac{\alpha}{2}P\right) \quad (3)$$

In Equation (3), Equation (1) and Equation (2) are substituted for PWV. From Equation (3), it can be appreciated that PPT is related to the Young's modulus of blood vessel, $\alpha$, which has a role for determining blood vessel elasticity, wherein the elastic modulus $\alpha$ can be calculated from the change of PTT according to the change of cuff pressure. That is, the PTT also increases when cuff pressure is applied as shown in FIG. 4, wherein the elastic modulus $\alpha$ is calculated by using the relationship between an increment of PTT in a cuff pressure applied area, and the cuff pressure. If the PTT increment is large for the same change in cuff pressure, the elastic modulus is also large. That is, it means the blood vessel elasticity is low. Thus, if the blood vessel elastic modulus can be calculated, it can be used as an indicator for blood vessel elasticity.

Accordingly, the control unit 550 calculates the cuff pressure at the time when pressure is applied by the cuff 510, the blood pressure at the time when the pressure is applied, and the increment in PTT at the time when the cuff pressure is applied. In other words, the control unit calculates the blood vessel elasticity, using the PTT at the time when no pressure is applied and the PTT at the time when pressure is applied.

Figure 6:
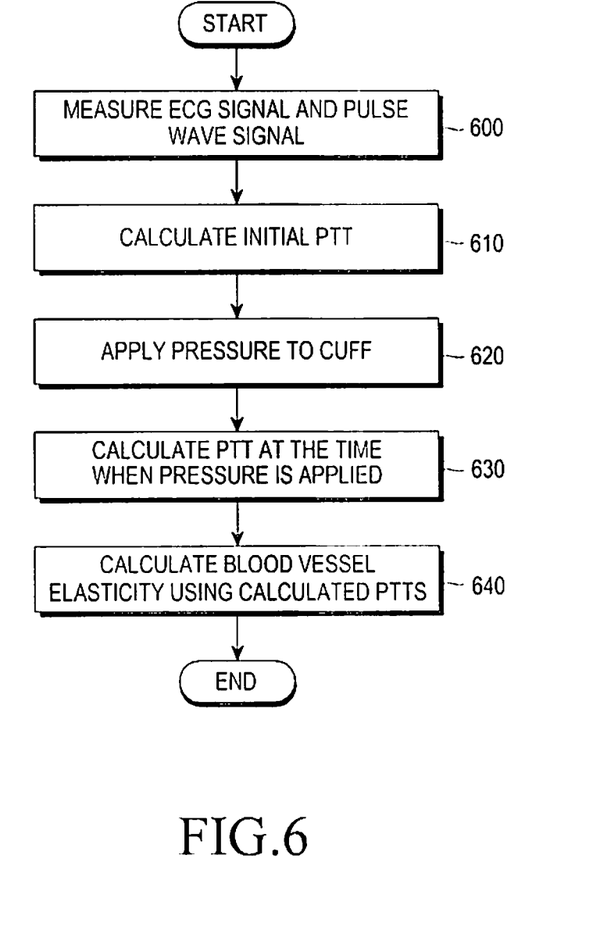
FIG. 6 is a flowchart illustrating the actions in the blood pressure measuring apparatus shown in FIG. 5.

The flowchart for the operations performed in this blood pressure measuring apparatus is shown in FIG. 6.

Figure 7A:
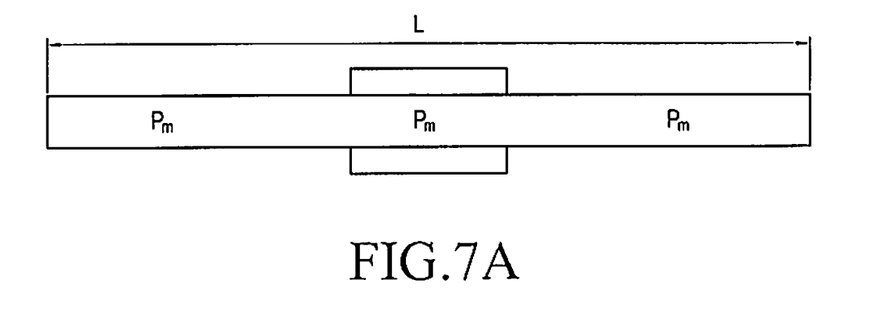
FIGS. 7a and 7b illustrate a method of calculating pulse transit time in accordance with an embodiment of the present invention.
Figure 7B:
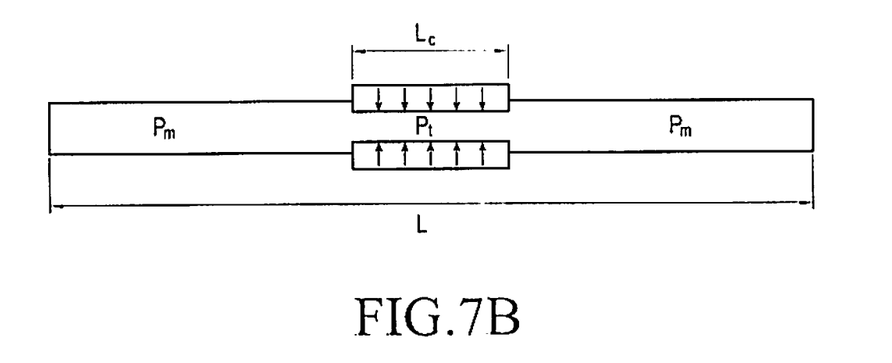

Referring to FIG. 6, after a heart beat signal and a pulse wave signal are measured in step 600, the initial PTT, i.e. $PTT_0$ is calculated in step 610, using the heartbeat signal and the pulse wave signal. FIGS. 7a and 7b show cases in which pressure is applied to an artery by a cuff, wherein the transmural pressure, i.e. the mean blood pressure of the artery is $P_m$, the blood vessel length of the artery is L, and the cuff length is $L_c$ (cm). FIG. 7a shows a method of calculating the initial PTT at a time when no pressure is applied to the cuff. The transmural pressure in the area surrounded by the cuff is equal to the mean blood pressure $P_m$, which is equal to the mean blood in the area that is not surrounded by the cuff. The mean blood pressure $P_m$ may be calculated from diastolic blood pressure and systolic blood pressure as in Equation (4) below.

$$P_m = P_d + k(P_s - P_d) \quad (4)$$

In Equation (4), $P_d$ is diastolic blood pressure, $P_s$ is systolic blood pressure, and k is a waveform coefficient. In general, 1/3 is used as the waveform coefficient.

$$PTT_o = L\sqrt{\frac{2\rho R}{E_o h}} \exp\left(-\frac{\alpha}{2}P_m\right) \quad (5)$$

In Equation (5), the artery length L is a distance from the heart to a fingertip where the pulse wave is measured. $E_0$ is the Young's modulus when the cuff pressure is zero, $\alpha$ is an elastic coefficient and hence a constant, $P_m$ is mean pressure, R is the blood vessel radius, h is blood vessel wall thickness, and $\rho$ is blood density. Here, the length L may be determined through a practical measurement, or by using a regression equation using the sex and height of a subject. Although the present invention is not so limited, an example of such a regression equation may be expressed like Equation (6) below.

$$L = 0.4861 \times \text{Height} + 0.6337 \text{ (cm)} \quad (6)$$

Equation (6) is a regression equation indicating the artery length from the heart to a finger of a Korean man.

Referring to Equation (5), if blood pressure is measured, it is possible to determine mean blood pressure through Equation (4), the mean blood pressure $P_m$ determined in this manner is substituted in Equation (5), and then the initial PTT ($PTT_0$) is calculated as in step 610, using the corresponding heart beat signal and pulse wave signal. Thereafter, the blood pressure measuring apparatus applies pressure to the cuff in step 620, and calculates PTT at the time when the pressure is applied in step 630.

FIG. 7b shows a method for calculating pulse transit time at the time when pressure is applied to the cuff. In FIG. 7b, if pressure is applied to the cuff, the pressure applied to the blood vessel at the cuff area is not $P_m$ but is converted to $P_t$, which corresponds to $P_m$ minus oppositely applied cuff pressure $P_c$. This may be expressed as Equation (7) below.

$$P_t = P_m - P_c \quad (7)$$

In Equation (7), $P_t$ is transmural pressure applied in the area where pressure is applied by the cuff, and $P_c$ is cuff pressure.

In the area $L_c$ where pressure is applied by the cuff, PTT increases since the cuff pressure increases. However, it is assumed that PTT in the remaining area of the entire length except the area $L_c$ is equal to the initial PTT ($PTT_0$). Thus, assuming that the increment of PTT in the area $L_c$ is $\Delta$, PTT may be expressed as Equation (8) below.

$$PTT_o + \Delta = (L - L_c)\sqrt{\frac{2\rho R}{E_o h}}\exp\left(-\frac{\alpha}{2}P_m\right) + L_c\sqrt{\frac{2\rho R}{E_o h}}\exp\left(-\frac{\alpha}{2}P_t\right) \quad (8)$$

In Equation (8), $\Delta$ is a function of Pt, which varies depending on the cuff pressure.

In Equation (8) above, the initial pulse transit time $PTT_0$ is the pulse transit time PTT when no pressure is applied, and $\Delta$ is the increment of PTT in the area $L_c$ where pressure is applied by the cuff, which varies depending on the cuff pressure, wherein the unit of $\Delta$ is msec. $\Delta$ is a measured value, which may be determined using the graph as shown in FIG. 4. Upon rearranging Equation (8), it is possible to obtain Equation (9) below.

$$-\ln\left(\frac{L_c}{L}PTT_o + \Delta\right) = \frac{\alpha}{2}P_t - \ln\left(L_c\sqrt{\frac{2\rho R}{E_o h}}\right) \quad (9)$$

In Equation (9) above, if a linear regression equation between the left term including the increment of PTT according to the cuff pressure, $\Delta$, and the blood pressure $P_t$ is determined, it is possible to determine the blood vessel elastic modulus $\alpha$. The blood vessel elastic modulus $\alpha$ may be expressed as Equation (10) below.

$$\alpha = \text{slope}\left(-2\ln\left(\frac{L_c}{L}PTT_o + \Delta\right), P_t\right) \quad (10)$$

In Equation (10), the slope function is a function expressing a slope obtained in a linear regression analysis of two variables. The blood pressure measuring apparatus calculates blood vessel elasticity as in Equation (10), using the PTTs calculated in step 640. If the change of PTT in terms of $P_t$ is measured by changing the cuff pressure, the blood vessel elastic modulus $\alpha$ can be determined through the regression analysis for the measured results.

As in Equation (10), the blood vessel elastic modulus $\alpha$ is determined by blood pressure at the area where pressure is applied by the cuff, the initial pulse transit time $PTT_0$, cuff length $L_c$, artery length L, and increment of PTT. Since the blood vessel elastic modulus $\alpha$ is determined by factors which can be commonly determined for various subjects, no individual variation is included in the blood vessel elastic modulus $\alpha$, which can be used as an absolute blood vessel elasticity indicator.

According to the present invention, it is possible to measure blood vessel elasticity of a subject simultaneously with measuring the blood pressure of the subject. This may be convenient for a subject. Additionally, the present invention can provide a method capable of measuring generally usable blood vessel elasticity, so that the blood vessel elasticity can be commonly applied to all of the subjects. Moreover, the present invention can be applied to a cardiovascular diagnosis or measuring apparatus since it does not rely on a blood pressure or individual variation.

While the invention has been shown and described with reference to certain embodiments thereof, it will be understood by those skilled in the art that various changes in form and details may be made therein without departing from the spirit and scope of the invention as defined by the appended claims and their equivalents.

What is claimed is:

1. A blood pressure measuring apparatus for measuring blood vessel elasticity, comprising:
    a Pulse Wave Velocity (PWV) measuring module for measuring PWV, using an electrocardiogram signal and a pulse wave signal;
    a blood pressure measuring module for measuring blood pressure by pressurizing or decompressing a cuff; and
    a control unit, wherein the control unit calculates an initial pulse transit time, using the PWV at a time when the cuff is not pressurized, wherein the initial pulse transit time is determined by dividing an arterial length from the heart to a pulse wave measuring point by the PWV, the control unit calculates pulse transit time in a pressure applied cuff area when the pressure is applied by the cuff, and the control unit calculates blood vessel elasticity, using the initial pulse transit time according to mean blood pressure in an area corresponding to the arterial length, a length of an area where pressure is applied by the cuff, the arterial length, a transmural pressure in the cuff area, and an increment of pulse transmit time in the cuff area according to the transmural pressure in the cuff area.

2. The apparatus of claim 1, wherein the PWV measuring module comprises:
    an electrocardiogram measuring unit for measuring the electrocardiogram signal; and
    a pulse wave measuring unit for measuring the pulse wave signal.

3. The apparatus of claim 1, wherein the blood pressure measuring module comprises:
    a cuff for pressurizing or decompressing an artery, the cuff being adapted to be wound on the upper part of an arm of a subject;
    an air pump for pressurizing the cuff;
    a pressure sensor for detecting pressure for pressurizing the cuff;
    an analog-digital converter for converting a signal from the pressure sensor to an electric signal; and
    a valve control unit for reducing the cuff pressure.

4. The apparatus of claim 1, wherein the initial pulse transit time is determined by dividing the arterial length from the heart to the pulse wave measuring point by the PWV, and Young's modulus of the artery is substituted for the PWV.

5. The apparatus of claim 4, wherein the blood pressure in the cuff area corresponds to mean blood pressure minus the pressure applied by the cuff.

6. The apparatus of claim 4, wherein the arterial length is determined by measuring the length from the heart to the pulse wave measuring point.

7. The apparatus of claim 4, wherein the arterial length is determined through a regression equation, using the sex and height of a subject.

8. The apparatus of claim 5, wherein the control unit calculates a blood vessel elastic modulus as the Young's modulus, using the initial pulse transmit time according to the mean blood pressure in an area corresponding to the arterial length, and the increment of pulse transmit time in the cuff area according to the blood pressure in the cuff area.

9. The apparatus of claim 8, wherein the blood vessel elastic modulus is expressed by, $$\alpha = \text{slope}\left(-2\ln\left(\frac{L_c}{L}PTT_o + \Delta\right), P_t\right)$$

wherein the slope function is a function expressing a slope obtained in a linear regression analysis of two variables, $P_t$ is transmural pressure in the cuff area, $PTT_0$ is the initial pulse transit time, $L_c$ is the area where pressure is applied by the cuff, L is the arterial length, and $\Delta$ is the increment of pulse transit time according to $P_t$ in the cuff area.

10. A blood pressure measuring method for measuring blood vessel elasticity by a blood pressure measuring apparatus, comprising:
   measuring Pulse Wave Velocity (PWV), using an electrocardiogram signal and a pulse wave signal;
   measuring blood pressure by pressurizing or decompressing a cuff;
   calculating an initial pulse transit time, using the PWV at a time when the cuff is not pressurized, wherein the initial pulse transit time is determined by dividing an arterial length from the heart to a pulse wave measuring point by the PWV;
   calculating pulse transit time in a pressure applied cuff area when the pressure is applied by the cuff; and
   calculating blood vessel elasticity, using the initial pulse transit time according to mean blood pressure in an area corresponding to the arterial length, a length of an area where pressure is applied by the cuff, the arterial length, a transmural pressure in the cuff area, and an increment of pulse transit time in the cuff area according to the transmural pressure in the cuff area.

11. The method of claim 10, wherein the initial pulse transit time is determined by dividing the arterial length from the heart to the pulse wave measuring point by the PWV, and Young's modulus of the artery is substituted for the PWV.

12. The method of claim 10, wherein the blood pressure in the cuff area corresponds to mean blood pressure minus the pressure applied by the cuff.

13. The method of claim 11, wherein the arterial length is determined by measuring the length from the heart to the pulse wave measuring point.

14. The method of claim 10, wherein the arterial length is determined through a regression equation, using the sex and height of a subject.

15. The method of claim 11, wherein calculating the blood vessel elasticity comprises:
   calculating a blood vessel elastic modulus as the Young's modulus, using the initial pulse transmit time according to the mean blood pressure in an area corresponding to the arterial length, and the increment of pulse transmit time in the cuff area according to the blood pressure in the cuff area.

16. The method of claim 15, wherein the elastic modulus of blood vessel is expressed by, $$\alpha = \text{slope}\left(-2\ln\left(\frac{L_c}{L}PTT_o + \Delta\right), P_t\right)$$

wherein the slope function is a function expressing a slope obtained in a linear regression analysis of two variables, $P_t$ is transmural pressure in the cuff area, $PTT_0$ is the initial pulse transit time, $L_c$ is an area where pressure is applied by the cuff, L is the arterial length, and $\Delta$ is the increment of pulse transit time according to $P_t$ in the cuff area.

* * * * *